(12) United States Patent
Petersen et al.

(10) Patent No.: US 7,135,876 B2
(45) Date of Patent: Nov. 14, 2006

(54) ELECTRICAL FEEDBACK DETECTION SYSTEM FOR MULTI-POINT PROBES

(75) Inventors: Christian Leth Petersen, Burnaby (CA); Peter Folmer Nielsen, Farum (DK)

(73) Assignee: Capres A/S, Lyngby (DK)

( * ) Notice: Subject to any disclaimer, the term of this patent is extended or adjusted under 35 U.S.C. 154(b) by 0 days.

(21) Appl. No.: 10/500,768

(22) PCT Filed: Jan. 7, 2003

(86) PCT No.: PCT/DK03/00006

§ 371 (c)(1),
(2), (4) Date: Feb. 11, 2005

(87) PCT Pub. No.: WO03/058260

PCT Pub. Date: Jul. 17, 2003

(65) Prior Publication Data

US 2005/0127929 A1    Jun. 16, 2005

(30) Foreign Application Priority Data

Jan. 7, 2002    (DK) .............................. 2002 00020

(51) Int. Cl.
*G01R 31/02*    (2006.01)
(52) U.S. Cl. ..................................... 324/756
(58) Field of Classification Search ..................... None
See application file for complete search history.

(56) References Cited

U.S. PATENT DOCUMENTS

| | | | | |
|---|---|---|---|---|
| 3,611,125 A | * | 10/1971 | Press et al. ................. 324/715 |
| 3,735,254 A | * | 5/1973 | Severin ....................... 324/716 |
| 3,995,213 A | * | 11/1976 | Robinson et al. ........... 324/715 |
| 4,887,025 A | * | 12/1989 | Re Fiorentin et al. ...... 324/693 |
| 5,136,252 A | * | 8/1992 | Witt ............................ 324/715 |
| 5,214,389 A | * | 5/1993 | Cao et al. ................... 324/719 |
| 5,525,911 A | * | 6/1996 | Marumo et al. ............ 324/754 |
| 5,583,446 A | * | 12/1996 | Takeuchi et al. ........... 324/754 |
| 5,627,522 A | | 5/1997 | Walker et al. |
| 6,091,248 A | | 7/2000 | Hellemans et al. |
| 6,154,041 A | * | 11/2000 | Cheng ........................ 324/758 |

FOREIGN PATENT DOCUMENTS

| | | |
|---|---|---|
| EP | 1085327 | 3/2001 |
| WO | 01/90730 | 11/2001 |

* cited by examiner

*Primary Examiner*—Vinh Nguyen
*Assistant Examiner*—Richard Isla-Rodas
(74) *Attorney, Agent, or Firm*—Altera Law Group, LLC

(57) ABSTRACT

An electrical feedback detection system for detecting electrical contact between a multi-point probe and an electrically conducting material test sample surface. The electrical feedback detection system comprises an electrical detector unit connected to a multitude of electrodes in the multi-point probe, and optionally directly to the test sample surface. The detector unit provides an electrical signal to a multi-point testing apparatus, which can be used to determine if the multi-point probe is in electrical contact with the test sample surface. The detector unit comprises an electrical generator means for generating an electrical signal that is driven through a first multitude of electrodes of the multi-point probe, and a second multitude of switched impedance detection elements. The electrical potential across the impedance detection elements determines the electrical contact to the test sample surface.

5 Claims, 8 Drawing Sheets

(a)

(b)

(a)

(b)

(a)

(b)

(a)

(b)

(a)

(b)

(a)

(b)

ELECTRICAL FEEDBACK DETECTION SYSTEM FOR MULTI-POINT PROBES

The present invention generally relates to an electrical feedback detection system for detecting physical contact and/or close proximity between a multi-point probe and an locally electrically conducting, semi-conducting or super-conducting material test sample surface and further relates to the technique of controlling the relative position of a multi-point probe and a material test sample surface, and in particular to an electrical feedback detection system for the multi-point probe and multi-point testing apparatus described in European Patent Application EP 98610023.8 (Petersen), International Patent Application PCT/DK99/00391 (Capres ApS et al), European Patent Application EP 99932677.0 (Capres ApS), European Patent Application EP 99610052.5 (Petersen et al), and International Patent Application PCT/DK00/00513 (Capres Aps et al).

DESCRIPTION OF THE RELATED ART

A scanning tunneling microscope involving controlled approach of a single tip electrode towards a conducting sample surface is well known from the literature; see for example Binnig and Rohrer, *Scanning tunneling microscopy*, Helv. Phys. Acta, vol. 55, pg. 355 (1982). The scanning tunneling microscope consists of a conducting sample and tip, as shown in FIG. 1(a). If the tip and the sample are separated by a very short distance d and a potential V exists between them, a tunneling current $$I \propto e^{-\sqrt{\phi} \cdot d},$$

is running between the tip and sample, $\phi$ being the average work function of the materials. If the distance d is on the order of 1 nm, a detectable current can be generated. FIG. 1(b) shows a schematic of a complete scanning tunneling apparatus capable of positioning the tip within tunneling distance from the test sample at different test locations, thereby generating maps of nanometer scale topographic and electrical features of the test sample.

FIG. 2(a)–(b) shows a schematic of the conventional four-point probe (see for example S. M. Sze, Semiconductor devices—Physics and Technology, Wiley New York (1985), and published international patent application WO 94/11745). The conventional four-point probe consists of four electrodes in an in-line configuration as shown in FIG. 2(a). By applying a current to the two peripheral electrodes, a voltage can be measured between the inner two electrodes. This allows the electric sheet resistivity of a test sample to be determined through the equation $$\rho = c \cdot (V/I),$$

wherein V is the measured voltage and I is the applied current and wherein c is a geometry factor determined by the electrode separation of the four-point probe and the dimensions of the test sample. A principle diagram of the electronic circuit connected to the four-point probe is shown in FIG. 2(b).

FIG. 3(a)–(b) shows a schematic of a conventional microscopic multi-point probe (se for example published European patent application EP 1 085 327 A1). FIG. 3(a) shows the multi-point probe, consisting of a supporting body and a multitude of conductive probe arms freely extending from the base of the supporting body. FIG. 3(b) shows a multi-point testing apparatus that implement the mechanical and electrical means for using the microscopic multi-point probe for measuring the electric properties of a test sample.

An object of the present invention is to provide a novel electrical detector mechanism allowing the detection of physical or otherwise electrical contact between a multi-point probe and a sample test material surface.

A particular advantage of the present invention is related to the fact that the novel electrical detector mechanism allows the detection of electrical connection between a multitude of multi-point probe electrodes, thereby giving information of the electrical contact of a multitude of electrodes of the multi-point probe.

A particular feature of the present invention is that the novel electrical detector mechanism does not require a macroscopically conducting sample surface, thereby providing detection of electrical contact to any material surface that contains a local electrical path between several electrodes of the multi-point probe at a specific location of the multi-point probe.

The above object, the above advantage and the above feature together with numerous other advantages and features which will be evident from the below detailed description of a preferred embodiment of the present invention is according to the present invention obtained by a electrical feedback control system for detecting electrical contact to a specific location of a test sample, comprising;
  (a) Electric generator means connected to a first multitude of electrodes of a multipoint probe;
  (b) A second multitude of switched impedance detection elements connecting said first multitude of electrodes of said multpoint probe; and
  (c) Electrical detector means for detecting a measuring signal from the electrical signal across said second multitude of switched impedance detection elements.

The technique characteristic of the present invention of detecting contact between a multi-point probe and the test locations of a test sample by utilizing an electrical signal flowing in the multi-point probe electrodes avoids the use of laser deflection detection mechanisms in the case of microscopic cantilever based multi-point electrodes, which is a dramatic simplification of the conventional optical feedback control systems for microscopic cantilever based testing apparatus such as Atomic Force Microscopes and Scanning Resistance Microscopes.

The electric generator means connected to a first multitude of multi-point probe electrodes according to the present invention sends a generator signal through the test sample at the test location, that being current or voltage, pulsed signal or signals, DC or AC having sinusoidal, square, triangle signal content or combinations thereof, ranging from LF to HF, in accordance with specific detection requirements such as sensitivity to resistance, inductance, capacitance or combinations thereof, having a LF sinusoidal AC current signal as the presently preferred embodiment.

The first multitude of electrodes of a multi-point probe according to the present invention ranges from at least two electrodes to 64 electrodes, having the two peripherally posotioned electrodes of the multi-point probe as the present preferred embodiment. Application of a generator signal to two peripherally positioned electrodes of the multi-point probe provides a resultant detector signal over the second multitude of impedance detection elements according to the present invention, and infers information about the electrical contact conditions of a third multitude of the multi-point probe electrodes. An electrical contact condition can involve physical contact, tunneling proximity, intermediate fluid meniscus, or any other effect allowing electrical current to flow between the multi-point probe electrodes and the test sample.

The second multitude of switched impedance detection elements according to the present invention ranges from one to ten, having three as the present preferred embodiment. The nominal values of the resistive part of the impedance detection elements ranges from 1 mΩ to 100 GΩ, having 1 kΩ, 10 kΩ and 100 kΩ as the presently preferred embodiment.

The electrical detector means measures an electrical signal across the second multitude of impedance detection elements according to the present invention, having a sensitive electrometer connected to a phase-locked lock-in amplifier as the preferred embodiment.

BRIEF DESCRIPTION OF THE DRAWINGS

Additional objects and features of the present invention will be more readily apparent from the following detailed description and appended claims taken in conjunction with the drawings, in which:

DETAILED DESCRIPTION OF THE PREFERRED EMBODIMENTS

Figure 1:
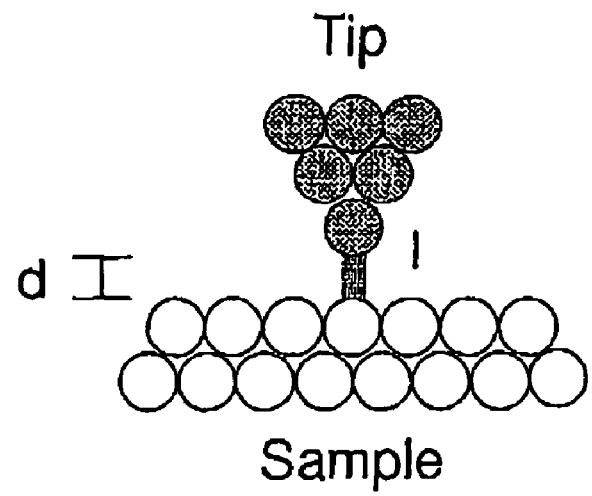
FIG. 1(a)–(b), provides an overall illustration of the conventional scanning tunneling microscope. (a), a schematic of the tunneling region between a conducting tip and a test sample. (b), a view schematically showing a conventional scanning tunneling apparatus.
Figure 1:
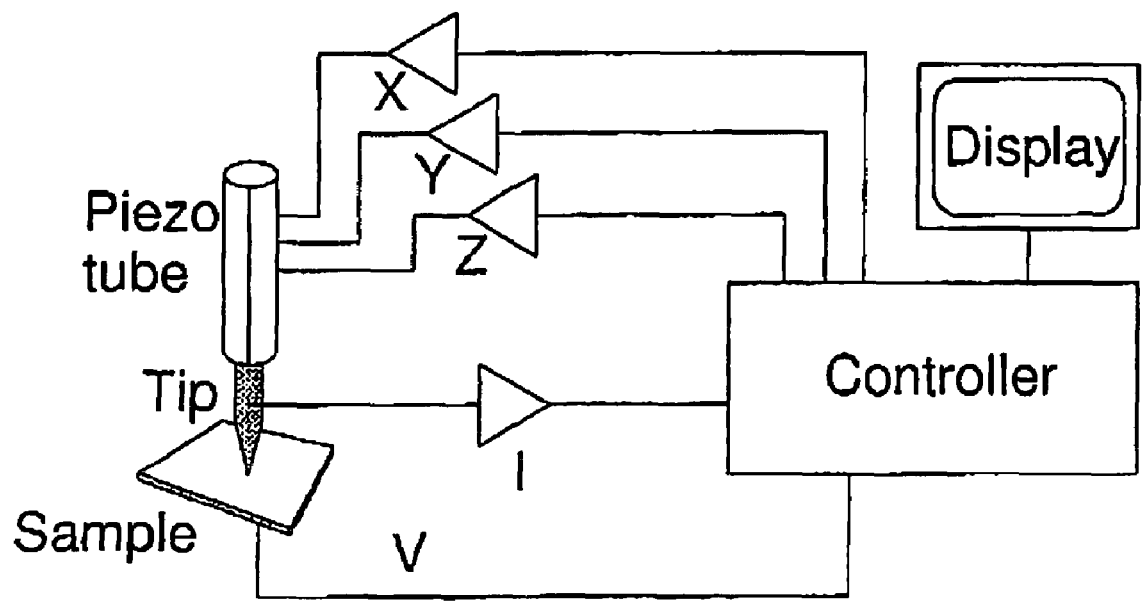
Figure 2:
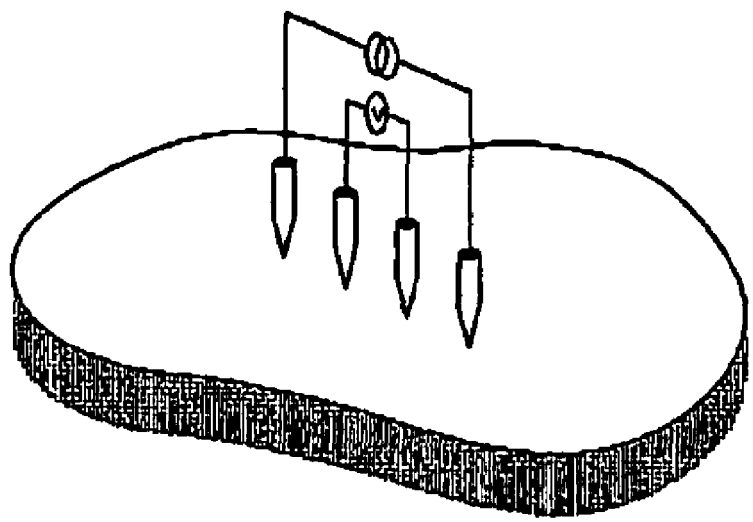
FIG. 2(a)–(b), provides a schematic illustration of the conventional four-point probe. (a), shows a schematic of a conventional four-point probe in electrical contact with a test sample. (b), shows an electrical schematic of a current source and electrometer connected to a conventional four-point probe.
Figure 2:
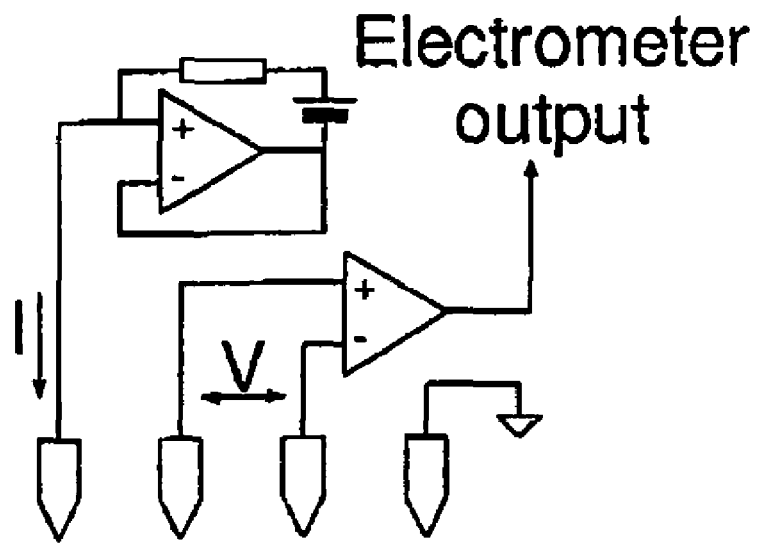
Figure 3:
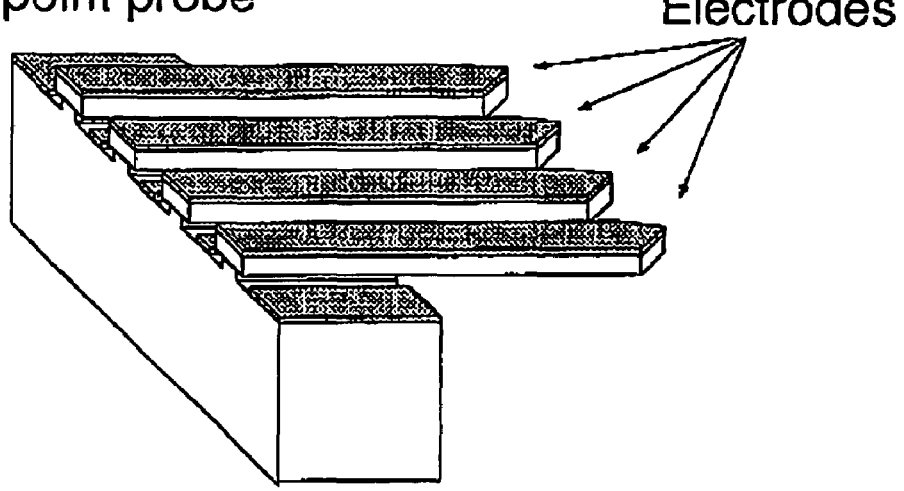
FIG. 3(a)–(b), shows an overall illustration of the conventional multi-point probe and testing apparatus. (a), shows the multi-point probe electrodes. (b), is a schematic of the multi-point testing apparatus.
Figure 3:
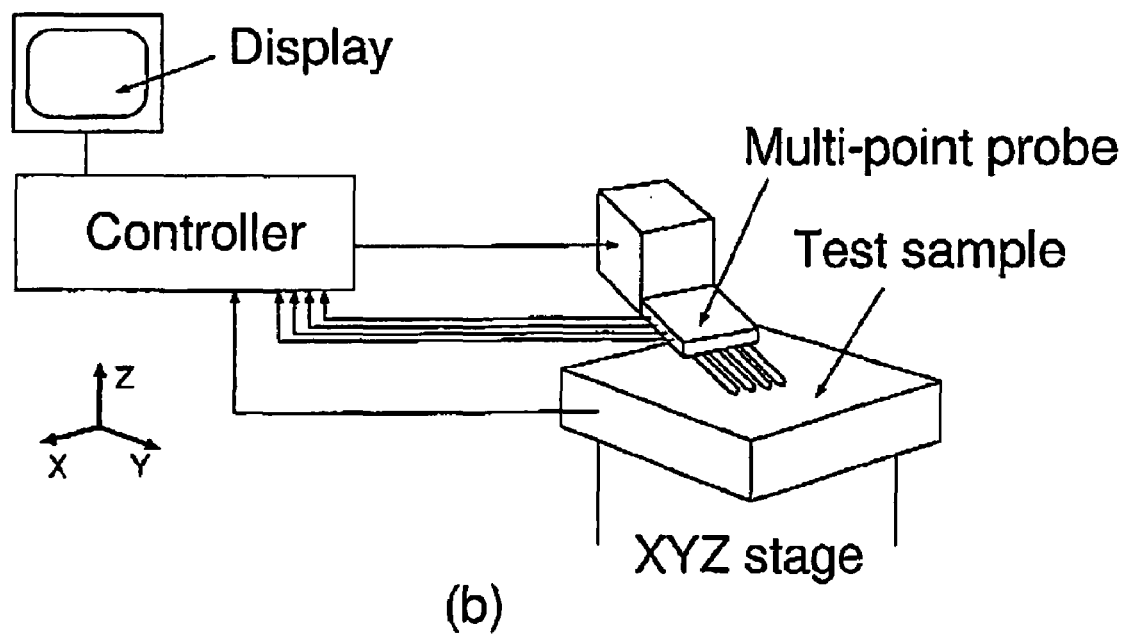
Figure 4:
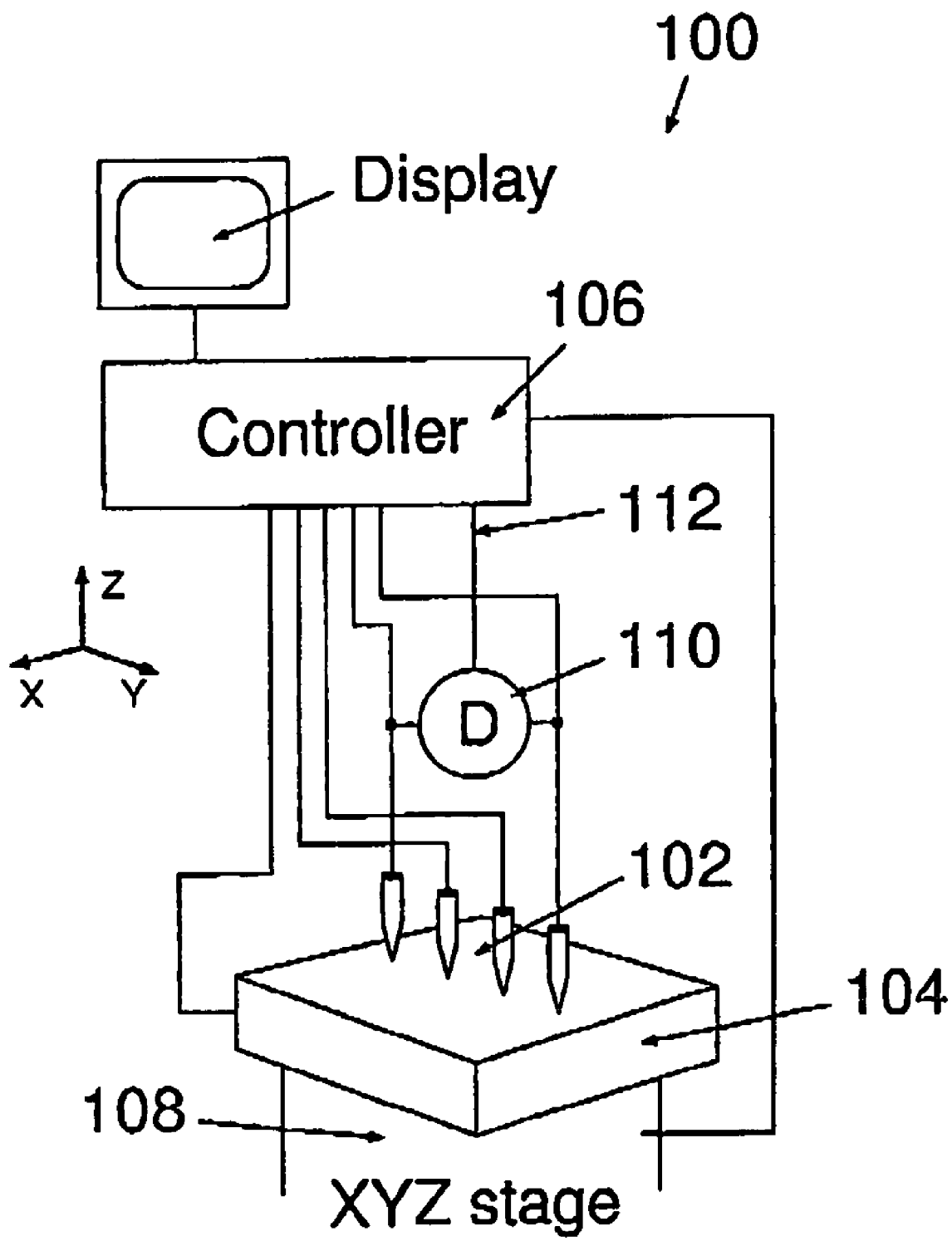
FIG. 4, shows a schematic view of the electrical feedback detection system according to the present invention.

A preferred embodiment is directed towards making an electrical feedback detection system for a multi-point probe and is described with respect to FIGS. 4–8. FIG. 4 shows a schematic of a multi-point testing apparatus 100 employing an electrical feedback detection system. The apparatus consists of a multi-point probe 102 in proximity to a test sample 104 which can be moved by a motor stage 108 by means of a controller 106. The peripherally positioned electrodes of the multi-point probe is connected to an electrical feedback detection system 110, which is capable of determining if the multi-probe 102 is in electrical contact with the test sample 104. A detector signal 112 is provided from the electrical feedback detection system 110 to the controller 106, to enable a controlled positioning and measurement with the multi-point probe 102 at test locations on the test sample 104.

FIGS. 5(a)–(b) and 6(a)–(b) together shows the principle of a preferred embodiment of the present invention. FIG. 5(a)–(b) shows a principle of the electrical configuration of the electrical feedback detection system 300 according to the invention, in a situation where no electrical contact exists between the multi-point probe 302 and the test sample 304. An electrical generator means generates a constant electrical current $I_c$, and is connected to the peripheral electrodes 302a and 302b of the multi-point probe 302. A impedance detection element consisting of resistive detection element R is connected to the circuit through closed switch SW, and the electrical potential $V_r$ across the resistive detection element R is measured by amplifier circuit A The equivalent electrical diagram of feedback detection system according to the invention in the situation depicted in FIG. 5(a), is shown in FIG. 5(b). The constant current $I_c$ runs through the resistive detection element R, thereby generating a potential difference $$V_r = R \cdot I_c,$$

Which is measured by amplifier A, and presented at the output of the feedback detection system. FIG. 6(a)–(b) shows a schematic diagram and equivalent circuit of the feedback detection system 500 in the case where the multipoint probe 502 is in electrical contact with the surface of the test sample 504. The electrical generator means is connected to the peripherally positioned electrodes 502a and 502b of the multi-point probe 502. A generated current $I_c$ flows in part through the closed switch SW and the resistive detection element R and the corresponding electrical potential $V_r$ is measured by the amplifier circuit A, and in part though the test sample 504 represented by unknown resistive element $R_x$. In this case the potential difference $V_r$ is $$V_r = (R \cdot R_x)/(R+R_x) \cdot I_c.$$

Figure 5:
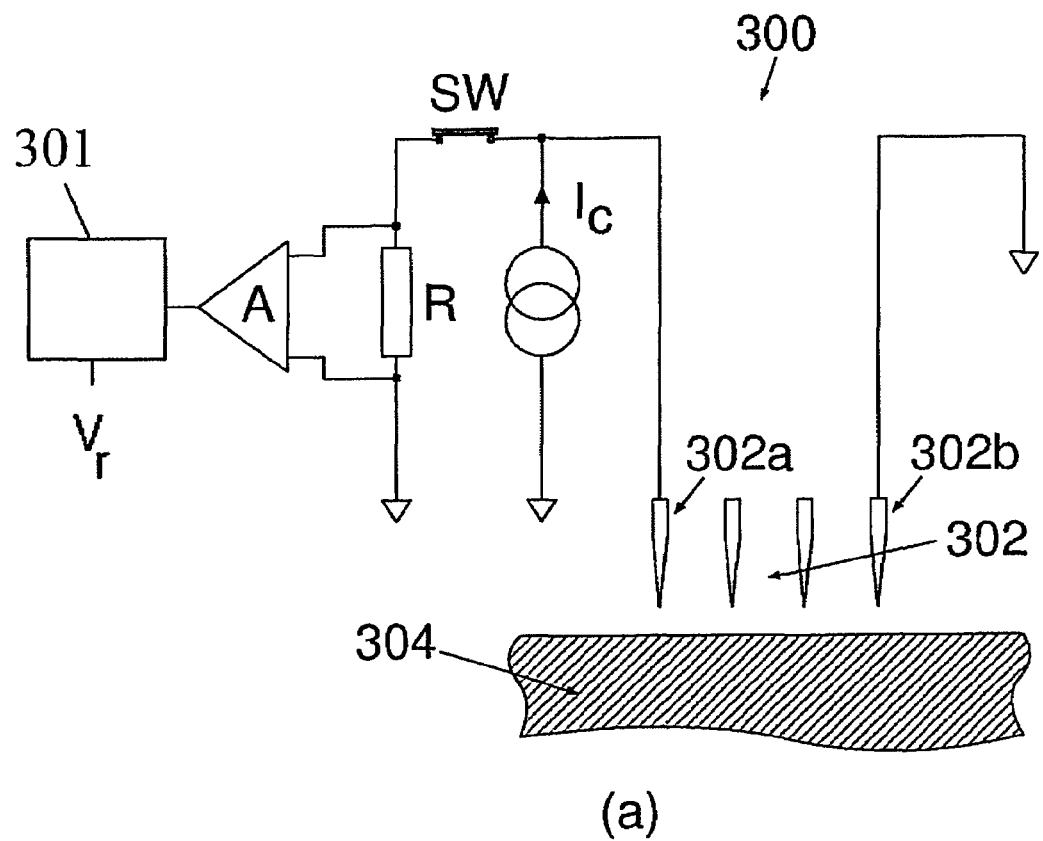
FIG. 5(a)–(b), shows an embodiment of the electrical feedback detection system according to the present invention, in which a multi-point probe is not electrically connected a test sample. (a), shows the detailed electrical configuration of the electrical feedback detection system. (b), shows the equivalent electrical diagram of the system.
Figure 5:
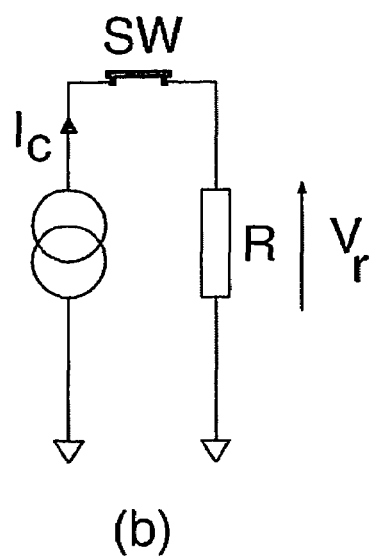
Figure 6:
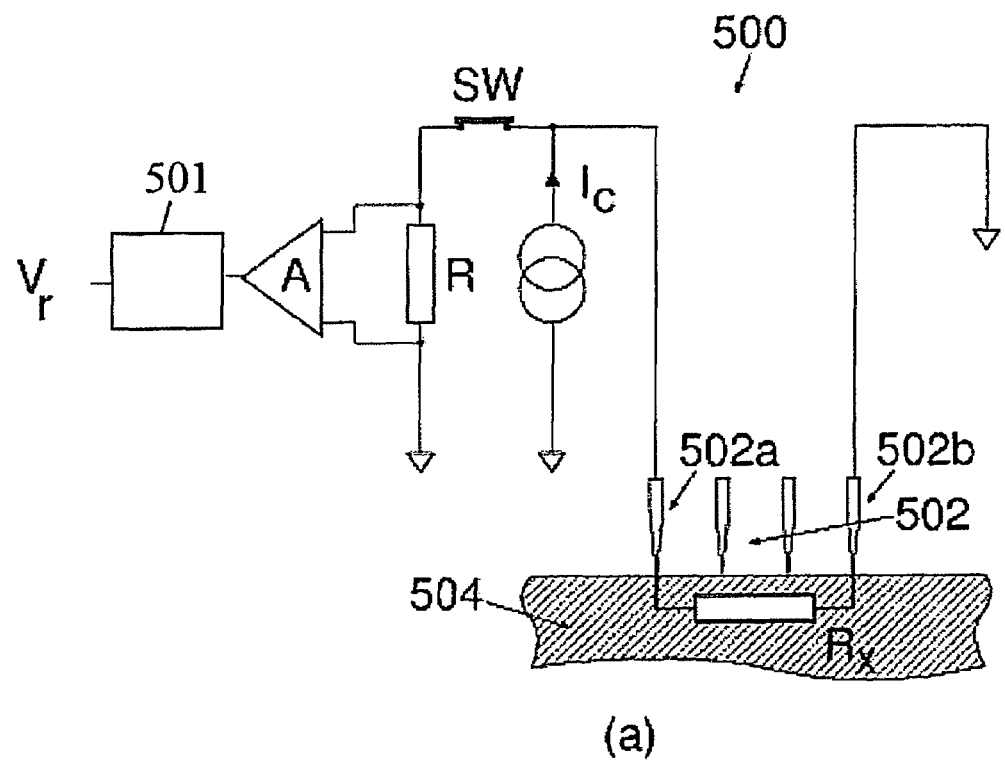
FIG. 6(a)–(b), shows an embodiment of the electrical feedback detection system according to the present invention, in which a multi-point probe is in electrical contact with a test sample. (a), shows the detailed electrical configuration of the electrical feedback detection system. (b), shows the equivalent electrical diagram of the system.
Figure 6:
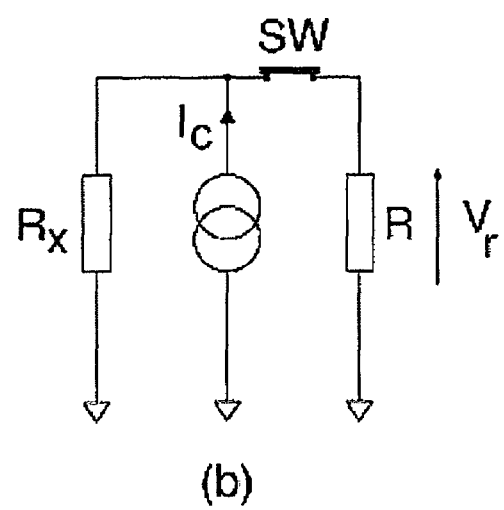
Figure 7:
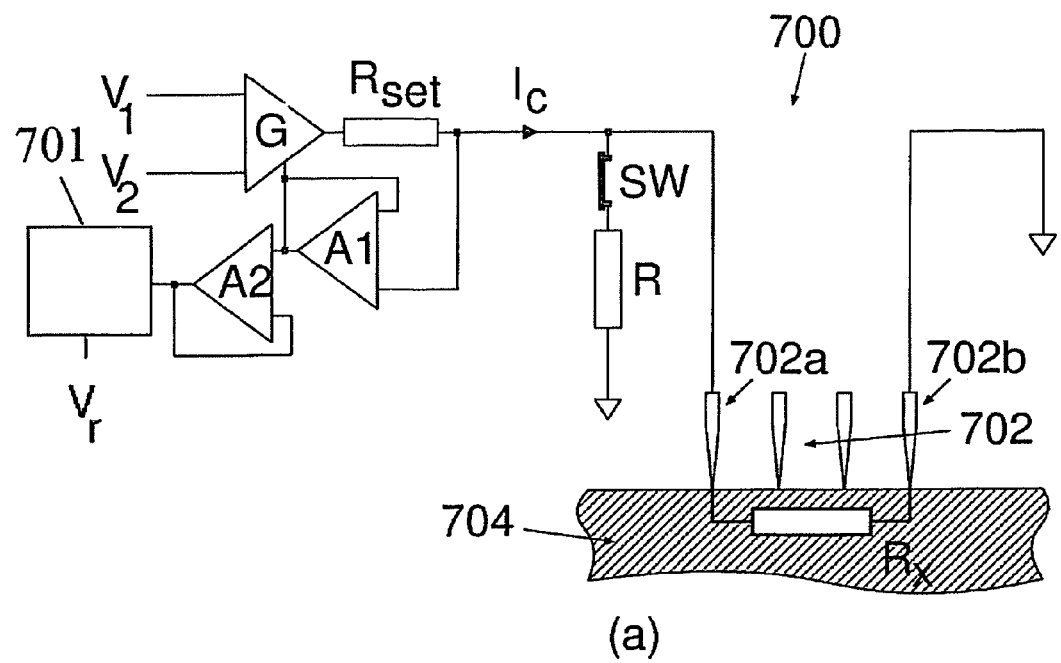
FIG. 7(a)–(b), shows embodiments of the electrical feedback detection system according to the present invention in which the feedback detection system includes a generator of constant electrical current. (a), shows a single switched impedance detection element in the control circuit. (b), shows a multitude of switched impedance detection elements in the control circuit.
Figure 7:
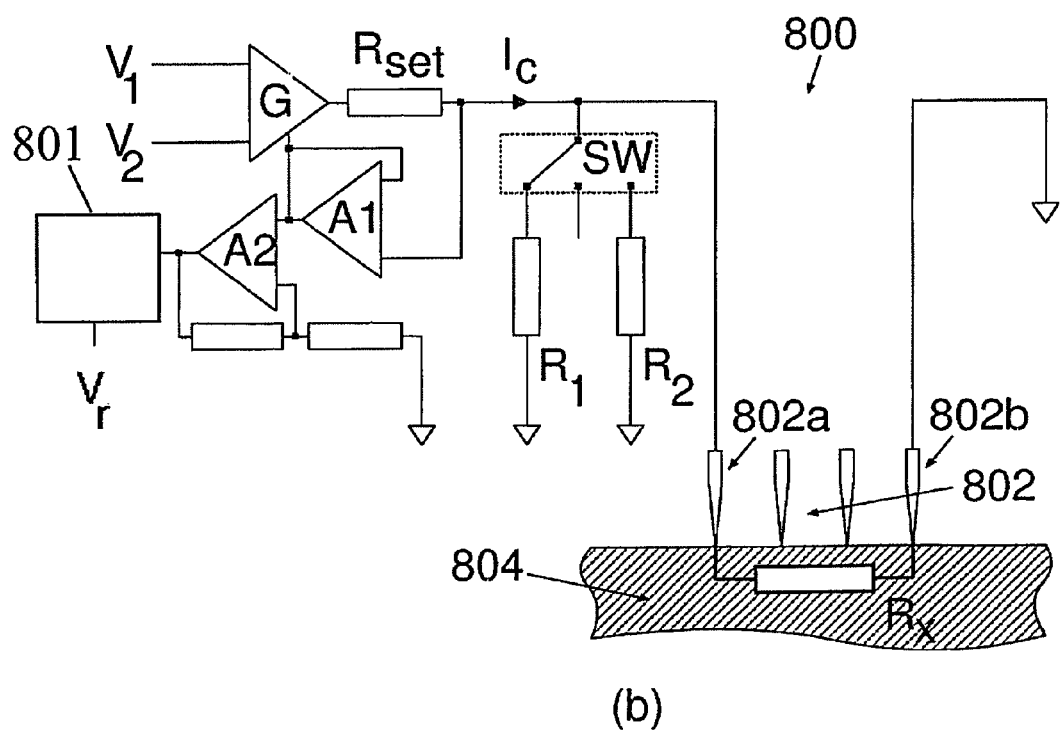

With reference to FIGS. 5 and 6 it is thus established that the introduction of electrical contact between a multi-point probe and a test sample generates a well-defined change in the output of the feedback detection system, hence allowing the detection of changes in the contact condition of a multi-point probe and a test sample.

In a preferred embodiment of the present invention the constant current generated by an electric generator means $I_c$ is 1 μA and the resistive detection element R has nominal value 100 kΩ, and hence the detector signal $V_r$ is 10V if no electrical contact is established between the multi-point probe and the test sample. If electrical contact exists to the test sample, the electrical properties of the test sample give rise to an effective resistance $R_x$ of the test sample. The following table shows the resulting detector signal $V_r$ for a range of different effective resistance values $R_x$ for the test sample:

| $R_x$ | $V_r$ | Relative change in $V_r$ from situation of no electrical contact |
|---|---|---|
| 10 Ω | 9.99 µV | 1,100,000 |
| 10 kΩ | 9.99 mV | 1,100 |
| 1 MΩ | 909 mV | 11 |
| 100 MΩ | 9.09 V | 1.1 |

This shows that the electrical feedback detection system is in this particular preferred embodiment of the present invention able to detect contact to test samples with effective electrical resistances in the range from 10Ω to 100MΩ. In a preferred embodiment of the present invention the detector signal is used by the controller of a multi-point testing apparatus to determine the electrical contact condition of a multi-point probe to a test location of a test sample, and to actively change the contact condition by means of electrical signals to a motor stage defining the relative position of the multi-point probe and the test sample.

FIG. 7(a)–(b) shows detailed implementations of preferred embodiments of the present invention. In FIG. 7(a), an electrical feedback detection system according to the invention 700 has the peripherally positioned electrodes 702a and 702b of a multi-point probe 702 connected to a differential voltage to current converter consisting of amplifier G, resistive detection element $R_{set}$ and voltage follower A1. The resistive detection element R is connected to the output of the voltage to current converter through switch SW. The output of the voltage to current converter is proportional to the voltage difference $V_1-V_2$. The detector signal $V_r$ is measured by means of amplifier A2. The current $I_c$ from the voltage to current converter is sent though the closed switch SW and the resistive detection element R and through the unknown effective resistance $R_x$ in the test sample 704. FIG. 7(b) shows an electrical feedback detection system according to the invention 800 with multi-point probe 802 connected to test sample 804 and electrical feedback detection circuit connected to the peripheral electrodes 802a and 802b of the multi-point probe 802. The electrical feedback detection circuit contains a multitude of resistive detection elements $R_1$ and $R_2$, which can be individually switched into the signal path of the electric generator means by means of switch SW, preferable application having three said resistive detection elements with nominal values in the range 100Ω to 10MΩ.

Figure 8:
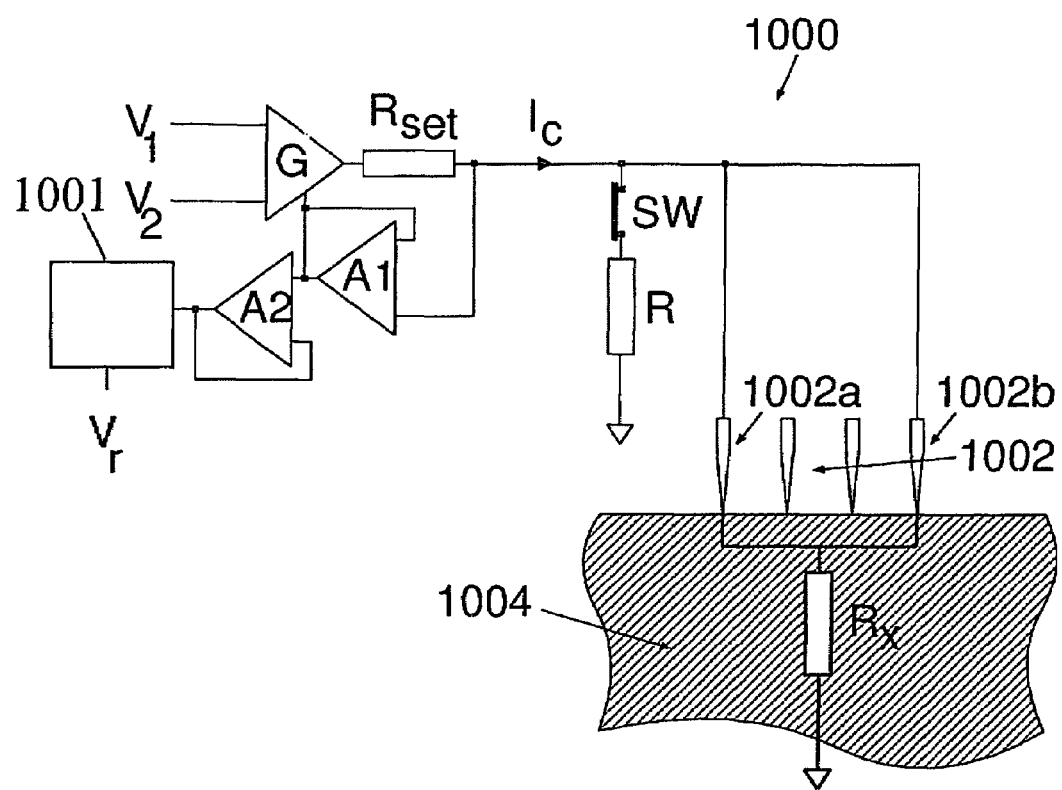
FIG. 8, shows an embodiment of the electrical feedback detection system according to the present invention in which the feedback detection system includes a generator of constant electrical current, and the detector signal is measured between a multitude of the multi-probe electrodes and the test sample material.

FIG. 8 shows another preferred embodiment of an electrical feedback detection system according to the present invention 1000, with multi-point probe 1002 connected to test sample 1004 and electrical feedback detection circuit connected between the peripheral electrodes 1002a and 1002b of the multi-point probe 1002, and test sample 1004. The generated current I runs in part through the test sample 1004, and this gives rise to a change in detector signal $V_r$ across a resistive detection element R, even when only one of the multitude of multi-point probe electrodes is in electrical contact with the test sample. FIGS. 5a, 6a, 7a, 7b and 8, include filters (301, 501, 701, 801, 1001) for filtering the output of the amplifier (A, A2).

The invention claimed is:

1. An electrical feedback detection system for detecting electrical contact of a multi-point probe to a material test sample surface comprising:
   a. electric generator means connected to a first multitude of electrodes of a multi-point probe;
   b. a second multitude of switched impedance detection elements connecting said first multitude of electrodes of said multi-point probe;
   c. electrical detector means connected to the output of the voltage follower for detecting a measuring signal from the electrical signal across said second multitude of switched impedance detection elements, and
   d. an electrical connection between said electric generator means to said material test sample surface, in which the electric generator means is a differential voltage to current converter comprising:
      e. a precision amplifier providing two differential inputs, one output, and one reference input;
      f. a precision resistive element providing an internal and external port, said internal port connected to said output of said precision amplifier; and
      g. the voltage follower providing an input and an output, said input connected to said external port of said precision resistive element, and said output connected to said reference input of said precision amplifier.

2. An electrical feedback detection system for detecting electrical contact of a multi-point probe to an electrically conducting material surface, comprising:
   i. electric generator means connected to a first multitude of electrodes of a multi-point probe, the electric generator means being a differential voltage to current converter comprising:
      a. a precision amplifier providing two differential inputs, one output, and one reference input;
      b. a precision resistive element providing an internal and external port, said internal port connected to said output of said precision amplifier; and
      c. a voltage follower providing an input and an output, said input connected to said external port of said precision resistive element, and said output connected to said reference input of said precision amplifier;
   ii. a second multitude of switched impedance detection elements connecting said first multitude of electrodes of said multi-point probe; and
   iii. electrical detector means connected to the output of the voltage follower for detecting a measuring signal from the electrical signal across said second multitude of switched impedance detection elements.

3. An electrical feedback detection system for detecting electrical contact of a multi-point probe to a electrically conducting material test sample surface according to claim 1, further comprising a filter for filtering the output of said electrical detector means, comprising a low-pass filter, high-pass filter, band-pass filter, comparator filter or any combinations thereof.

4. An electrical feedback detection system for detecting electrical contact of a multi-point probe to an electrically conducting material test sample surface according to claim 1 in which said multi-point probe comprises:
   a. a supporting body defining a first surface; and
   b. a first multitude of conductive probe arms each of said conductive probe arms defining a proximal end and a distal end being positioned in co-planar relationship with said first surface of said supporting body, and said conductive probe arms being connected to said supporting body at said proximal ends thereof and having said distal ends freely extending from said supporting body, giving individually flexible motion to said first multitude of conductive probe arms.

5. A multi-point testing apparatus for testing electric properties on a specific location of a test sample, comprising:
   a. An electrical feedback detection system according to claim 1;
   b. means for receiving and supporting said test sample; and
   c. wherein said electric generator means includes means for generating a test signal and electric measuring means for detecting a measuring signal.

* * * * *